United States Patent [19]

Parker et al.

[11] Patent Number: 4,592,361
[45] Date of Patent: Jun. 3, 1986

[54] ELECTRO-OPTICAL DEVICE AND METHOD FOR MONITORING INSTANTANEOUS SINGLET OXYGEN CONCENTRATION PRODUCED DURING PHOTORADIATION USING PULSED EXCITATION AND TIME DOMAIN SIGNAL PROCESSING

[75] Inventors: John G. Parker, Olney; William D. Stanbro, Columbia, both of Md.

[73] Assignee: The Johns Hopkins University, Baltimore, Md.

[21] Appl. No.: 629,879

[22] Filed: Jul. 11, 1984

Related U.S. Application Data

[63] Continuation-in-part of Ser. No. 393,188, Jun. 28, 1982, abandoned.

[51] Int. Cl.[4] .......................... A61B 6/00; A61N 5/00
[52] U.S. Cl. .................................. 128/633; 128/634; 128/654; 128/664; 128/362; 128/635
[58] Field of Search ...................... 128/362, 395, 303.1, 128/633, 634, 654, 665, 396-398, 664, 635

[56] References Cited

U.S. PATENT DOCUMENTS 3,136,310  6/1964  Meltzer ............................. 128/634
4,336,809  6/1982  Clark ................................ 128/665

OTHER PUBLICATIONS

Krasnovsky, Biofizaka, vol. 21: No. 4, 1976, pp. 770–771.
Khan et al., Proc. Natl. Acad. Science, vol. 76(12), Dec. 1979, pp. 6047–6049.
Salokhiddinov et al., Chem. Phys. Letters, vol. 76, No. 1, Nov. 15, 1980, pp. 85–86.
Krasnovsky, Photochemistry and Photobiology, vol. 29, 1979, pp. 29–36.
Sedden et al., Int. J. Radiat. Phys. Chem., vol. 5, 1973, pp. 323–328.
Parker et al., Presentation, Clanton Foundation Symposium, Apr. 24–28, 1983.
Kinsey et al., Rev. of Scientific Instru., vol. 51(10), Oct. 1980, pp. 1403–1406.
Doiven et al., Chest, vol. 76:1, Jul. 1979, pp. 27–32.
Dougherty et al., Cancer Research, vol. 38, Aug. 1978, pp. 2628–2635.
Parker et al., J. Amer. Chem., Soc., vol. 104, 1982, pp. 2067–2069.

Primary Examiner—Kyle L. Howell
Assistant Examiner—John C. Hanley
Attorney, Agent, or Firm—Robert E. Archibald; Howard W. Califano

[57] ABSTRACT

A method and apparatus is disclosed for optically monitoring the concentration of singlet oxygen produced during photoradiation. A composite optical emission in the 1.27 micron frequency band is detected and electrically processed to separate a first component due to the decay of singlet oxygen from a second unwanted component due to the fluorescence of the photosensitizing dye.

A pulsed excitation source is used to excite the photosensitizing dye and a time domain signal processor, such as a box-car integrator, is used to separate and process the singlet oxygen emission component in the time domain.

The magnitude and/or other characteristics of the singlet oxygen emission component can be used to determine properties of complex biological or other media. In a therapeutic environment the magnitude and/or other characteristics of the singlet oxygen emission can be used by the treating physician to set a therapeutic light dosimetry.

80 Claims, 11 Drawing Figures

ELECTRO-OPTICAL DEVICE AND METHOD FOR MONITORING INSTANTANEOUS SINGLET OXYGEN CONCENTRATION PRODUCED DURING PHOTORADIATION USING PULSED EXCITATION AND TIME DOMAIN SIGNAL PROCESSING

STATEMENT OF GOVERNMENTAL INTEREST

The Government has rights in this invention pursuant to Contract No. N00024-81-C-5301 awarded by the Department of the Navy.

CROSS-REFERENCE TO RELATED APPLICATION

This is a continuation-in-part of patent application, Ser. No. 393,188, filed on June 28, 1982 now abandoned.

BACKGROUND OF THE INVENTION

1. Field of the Invention

This invention relates to an apparatus and method for processing and monitoring the instantaneous concentration of singlet oxygen produced during photoradiation when a pulsed excitation source is used to excite a photodynamic sensitizer.

2. Background and Technical Summary

When certain photodynamic sensitizers, such as hematoporphyrin derivative, are injected intraveneously into the human body, they are selectively retained by cancerous tissue. Thus, two or three days after injection, significantly higher levels of the photodynamic sensitizer are retained in malignant tissue. The selective retention of hematoporphyrin derivative by cancerous tissue was first used clinically as a diagnostic tool. In the presence of ultraviolet or shortwave length visible light, such tissue will exhibit a bright red fluoroscence while normal tissue appears light pink. A discussion of clinical investigations using this diagnostic technique can be found in an article entitled "Hematoporphyrin Diacetate: A Probe to Distinguish Malignant from Normal Tissue by Selective Fluoroscence" by R. W. Henderson, G. S. Christie, P. S. Clezy and J. Lineham, *Brit. J. Exp. Pathol.*, Vol. 61, pages 325–350 (1980). Another reference by D. R. Doiron and A. E. Profio entitled "Laser Fluorescence Bronchoscopy for Early Lung Cancer Localization" published in *Lasers in Photomedicine and Photobiology* (1980) teaches the use of a laser fluorescence bronchoscope to detect and localize small lung tumors by observing this red fluorescence.

An additional clinical application has recently been found in the treatment and destruction of malignant tissue, i.e., photochemotherapy or photoradiation therapy. The process by which biological damage occurs, as the result of optical excitation of a hematoporphyrin dye in the presence of oxygen, is generally referred to as "photodynamic action". As indicated above, photochemotherapy involves the injection of a hematoporphyrin dye intravenously into the patient. After the passage of several days, usually three, the dye is retained in significant amounts by cancerous tissue, however being eliminated by healthy tissue. The tumor is then exposed to a therapeutic light and this light energy causes the photodynamic sensitizer to be excited to an energetic metastable triplet state. Through a direct intramolecular process, the dye transfers energy to oxygen molecules present in the tissue and raises them from the ground triplet to the first excited electronic singlet state, $^1O_2$. The singlet oxygen, $^1O_2$, attacks and functionally destroys the cell membranes ultimately inducing necrosis and destroying the cancerous tissue.

In an article by Thomas J. Dougherty et al entitled "Photoradiation Therapy for the Treatment of Malignant Tumors" published in *Cancer Research*, Vol. 38, pages 2628–2635 (1978), problems associated with prescribing the correct therapeutic light dosages are discussed. If the dosage is too weak, the tumor response will be partial or incomplete. If the irradiation time is too long or intensity too high, normal skin or tissue will experience necrosis. The aforementioned article points out the difficulty of determining the correct therapeutic dosage of light. This problem has been proven to be quite significant and currently is one of the major hurdles that must be overcome before photochemotherapy can be used to systematically and reliably treat tumors.

Other clinical applications of photoradiation therapy are being investigated which also point out the urgent need to develop an apparatus and method for monitoring the instantaneous generation of singlet oxygen.

SUMMARY OF THE INVENTION

The inventors recognized the need to measure the generation of singlet oxygen in a biological environment produced during photoradiation therapy. They recognized that adequate photoradiation treatment is questionable unless one knows directly the rate at which singlet oxygen is generated in the biological or malignant tissue. The inventors recognized that the generation of singlet oxygen involves several key factors: (1) the therapeutic light source must be of the proper intensity and wavelength sufficient to elevate the photodynamic sensitizer to an excited singlet state; (2) there must be a sufficient concentration of oxygen localized within the tumor both initially and during the period of irradiation to be excited by energy transfer from the sensitizer; (3) the local sensitizer concentration may very considerably, depending on the hydrophobic or hydrophilic nature of the immediate environment; and (4) the rate of quenching of $^1O_2$ may vary substantially with the existing medium, being generally more rapid in an aqueous than in a liquid environment. Therefore, merely measuring the incident light intensity and time of exposure, as is taught by the prior art, will not supply adequate information regarding the generation of singlet oxygen within the tumor tissue. The inventors, therefore, recognize the need to determine directly the amount of singlet oxygen which is being generated during photoradiation therapy.

The inventors recognize that direct monitoring of the generation of $^1O_2$ is possible because in the interaction of singlet oxygen molecules with the surrounding medium, the singlet oxygen molecules undergo a collisionally-induced radiative transition to ground triplet state emitting light at a wavelength of 1.27 microns, e.g., J. G. Parker and W. D. Stanbro, "Optical Determination of the Collisional Lifetime of Singlet Molecular Oxygen $[O_2{}^1\Delta_g]$ in Acetone and Deuterated Acetone", *J. Am. Chem. Soc.*, Vol. 104, pp 2067–2069 (1982). Singlet oxygen emission in liquids was first described in an article by A. A. Krasnovsky, Jr. entitled "Photosensitized Luminescence of Singlet Oxygen in Solution" reprinted in *Biophysics* (GB), Vol. 21, page 770 (1976). Krasnovsky is generally recognized as the first to identify and optically detect the singlet oxygen emission at 1.27 microns in solution. Krasnovsky used a cryogenically cooled photomultiplier as the means for detecting this emission in a CCl₄ solvent. Additional work has been done for various other solvents, e.g., A. H. Khan and M. Kasha, "Direct Spectroscopic Observation of Singlet Oxygen Emission at 1268 nm, Excited by Sensitizing Dyes of Biological Interest in Liquid Solution", *Proc. Natl. Acad. Science.*, Vol. 76(12), page 6047 (1979); and K. I. Salokhiddinov, B. N. Dzhagarov, I. M. Byteva, and G. P. Gurinovich, "Photosensitized Luminescence of Singlet Oxygen in Solutions at 159 nm", *Chem. Phys. Lett.*, Vol. 76(1), page 85 (1980). To detect the 1.27 micron emission Khan et al used a near-infrared spectrophotometer that employed a thermoelectrically cooled lead sulfide detector and Salokhiddinov et al used a liquid nitrogen cooled germanium photodiode.

However, these prior researchers measured the singlet oxygen emission in solvents, such as carbon tetrachloride CCl₄ where the lifetime of singlet oxygen is extremely long—approximately 28,000 microseconds. The more difficult problem, which the present invention have addressed, is how to optically detect and electronically process singlet oxygen emissions generated in a biological environment. In a biological environment, composed essentially of water and lipids (hydrocarbons), the singlet oxygen lifetime is extremely short, ranging from 3 (water) to 30 (lipid) microseconds. The present invention provides an apparatus and method for detecting the singlet oxygen emission produced during photoradiation therapy in a biological environment.

To fully understand the problem, it is essential to recognize that both the photodynamic sensitizer and the singlet oxygen molecules produce emissions having wavelengths in the region of 1.27 microns. Results of experimental measurements made by the present inventors indicate that singlet oxygen emission and the sensitizer fluorescence both arise as a consequence of optical excitation of the sensitizer and are inextricably intertwined. Therefore, a composite two component emission is produced having: (1) a first spectrally discrete component attributed to singlet oxygen emissions; and (2) a second spectrally diffuse component produced by fluorescence of the sensitizer. Even if a narrow band pass filter centered at 1.27 microns were used both the sensitizer fluorescence and the singlet oxygen emission would be transmitted to the photodetector. The desired singlet oxygen emission signal *cannot be spectrally separated* from the composite sensitizer fluorescence/singlet oxygen emission signal. (The infrared fluorescence produced by the sensitizer ranges from a wavelength of 0.70 microns to wavelengths in excess of 1.50 microns.)

The central difficulty to be overcome, therefore, in monitoring the singlet oxygen emission is to separate the singlet oxygen emission component from the component due to sensitizer fluorescence. To accomplish this task one must exploit the different nature of the two signal components. The inventors have found that the sensitizer fluorescence occurs simultaneously with the pulsed excitation light while the appearance of the singlet oxygen emission is delayed in time. The inventors discovered that this delay is due to the fact that formation of singlet oxygen is not directly coupled to the optical excitation. Formation of singlet oxygen involves a collisional transfer of energy from the sensitizer metastable triplet state, and is thus delayed with respect to the initiation of the optical excitation by the time required to bring about collision of the ground electronic state dissolved oxygen ³O₂ with the photodynamic sensitizer.

The problem of extracting the singlet oxygen emission signal from the composite sensitizer fluorescence/singlet oxygen emission signal, is extremely complex in a biological environment. First, the sensitizer fluorescence is in general much larger than the singlet oxygen emission, e.g., having a magnitude 20 times that of the singlet oxygen emission in an aqueous medium. The weakness of the singlet oxygen emission in an aqueous environment is attributed to the short lifetime of singlet oxygen. In lipid environments, the ¹O₂ lifetimes are significantly longer and the magnitudes of the infrared fluorescent component tends to be relatively smaller. Secondly, the time delay between the sensitizer fluorescence and the singlet oxygen emission is dependent on the diffusion rate of ³O₂ for each particular solvent. In a biological environment comprised of essentially water and lipids the delay varies from 2–3μ sec for water to times approaching 10μ sec for glycerol and ethylene glycol (characteristic of cell membrane environments) and various serums.

Therefore, in a biological medium, the sensitizer fluorescence is in general much larger in magnitude than a singlet oxygen emission; the time delay between the appearance of the sensitizer fluorescence and the peak of the singlet oxygen emission is relatively short (2.5 to 10.0 microseconds); and, the overall lifetime of singlet oxygen is can be extremely short (e.g., 3.1μ sec in aqueous regions).

The inventors recognized that, in such a biological environment, if one merely measures the optical emission in a narrow band centered at 1.27 microns (i.e., the singlet oxygen 1.27 micron emission band), one will essentially be measuring a fluorescent signal generated by the sensitizer and *not* the singlet oxygen emission.

The present inventors have developed a method and apparatus for extracting the singlet oxygen emission signal from the composite sensitizer fluorescence/singlet oxygen emission signal, both of which appear in the 1.27 micron singlet oxygen emission band. The invention generally includes: a pulsed excitation signal used to radiate a biological mass which has absorbed a photodynamic sensitizer such as hematoporphyrin derivative; an optical detection means including a light collection means, filter means and photodetector means all for detecting the *composite* emission signal produced in the 1.27 micron singlet oxygen emission band; and, a time domain processing means including a box-car integrator or signal averager connected to the photodetector and triggered at the pulsing rate of the excitation signal.

The inventors discovered that the composite sensitizer fluorescence/singlet oxygen emission signal can be resolved in the time domain by taking advantage of the fact that the sensitizer fluorescence occurs essentially concurrently with the excitation pulse, whereas the singlet oxygen emission is delayed. When a box-car integrator performs the temporal discrimination function, the sampling interval of the box-car integration can be delayed so as to extract the delayed singlet oxygen signal. The inventors have found that a minimum delay time of 1–1.5μ sec. should be imposed in a biological environment to avoid any interference with the sensitizer fluorescence. Alternatively, a signal averager can be used to provide the temporal discrimination by analyzing the total time history and discarding the initial 1.0–1.5μ sec. dominated by the sensitizer fluorescence. In general, the present invention teaches that to extract the singlet oxygen emission signal from the composite signal one needs: (1) an optical detector with a fast return response, so that it can recover from the larger sensitizer fluorescence signal; and, (2) a time domain processor (such as a box-car integrator, or signal averager) to temporally discriminate and isolate the delayed singlet oxygen emissions.

The present invention also provides a means for detection of a maximum singlet oxygen signal generated in a complex heterogeneous biological environment composed of both aqueous and lipid media. By adjusting the aperture width and delay of a box-car integrator, and by scanning the aperture across a range of values one may determine the maximum singlet oxygen signal generated in a complex environment. Alternatively, a signal averager in combination with processing software can identify the time bin (address) containing the maximum singlet oxygen signal. The time domain processor can also be preset to determine the maximum singlet oxygen signal which is generated in a particular environment (i.e., the time domain signal processor can be set at a particular delay to extract the maximum singlet oxygen signal generated in a lipid environment, and a second preset delay to extract the singlet oxygen signal generated in an aqueous environment).

The present inventors thus recognize that optical excitation of the photodynamic sensitizer during photoradiation produces a composite two-component signal; a first component due to the singlet oxygen emission; and, a second larger component due to sensitizer infrared fluorescence. Recognizing that a narrow band-pass filter centered to pass the 1.27 micron signal oxygen emission band, will pass both the desired singlet oxygen emission signal and the stronger undesired signal due to the sensitizer fluorescence, the present inventors have developed an apparatus and method for isolating the singlet oxygen emission signal by time domain signal processing.

One novel feature of the invention is the use of time domain signal processing to separate the singlet oxygen emission signal from a composite sensitizer fluoroescence/singlet oxygen emission signal produced during photoradiation.

A second novel feature is the use of pulsed excitation in combination with a time domain signal processor. The excitation can be pulsed and the time domain signal processor triggered synchronously, in order to separate the singlet oxygen emission from the composite signal dominated by sensitizer fluorescence.

A third novel feature of the invention is the use of a box-car integrator to extract the singlet oxygen emission signal from the sensitizer fluorescent signal. The box-car integrator can be further used to temporally distinguish between singlet oxygen emissions generated in different biological environments. The time domain processing means as taught by the present invention includes a box-car integrator having an adjustable aperture delay which can be set to temporally distinguish the desired singlet oxygen emission signal from the composite sensitizer fluorescence/singlet oxygen signal.

A fourth novel feature is the use of a box-car integrator in conjunction with a computing means to determine the maximum singlet oxygen emission in a complex multi-component environment—such as biological mass. The computing means periodically analyzes the box-car integrator output for a preset range of aperture delay values to assure that the maximum singlet oxygen signal is being retrieved.

A fifth novel feature is the use of a box-car integrator in conjunction with a computing means to analyze certain properties of a complex medium, and to detect the singlet oxygen emission peaks attributable to different components.

A sixth novel feature is the use of a signal averager to process the composite sensitizer fluorescence/singlet oxygen emission signal in the time domain and extract the singlet oxygen signal. Further, data accumulated in the plurality of time bins (address) in the signal averager can be used to provide a time history of the singlet oxygen emission signal.

A seventh novel feature is the use of a signal averager in conjunction with a computing means to calculate the total or peak singlet oxygen concentration in a complex multi-component environment, such as biological mass. The computing means utilizes a regression analysis of the singlet oxygen emission time history to calculate the total or peak singlet oxygen emission.

An eighth novel feature is the use of a computing means in conjunction with a time domain processing means to control the intensity and modulation of the excitation pulses as a function of measured singlet oxygen level. During photochemotherapy the critical excitation light dosage can be controlled to assure that singlet oxygen is being produced at an acceptable level.

A ninth novel feature of the invention is that it provides a means for remotely monitoring the instantaneous singlet oxygen concentration produced during photoradiation therapy when a pulsed light source acts as the excitation beam. By monitoring the singlet oxygen level, the physician or operator can adjust the therapeutic irradiation conditions (i.e., intensity, wavelength, angle of incidence, time of exposure, etc.) to provide a singlet oxygen level as necessary to satisfy predetermined clinical conditions and to minimize the effects of oxygen depletion.

DESCRIPTION OF THE PREFERRED EMBODIMENTS

Figure 1:
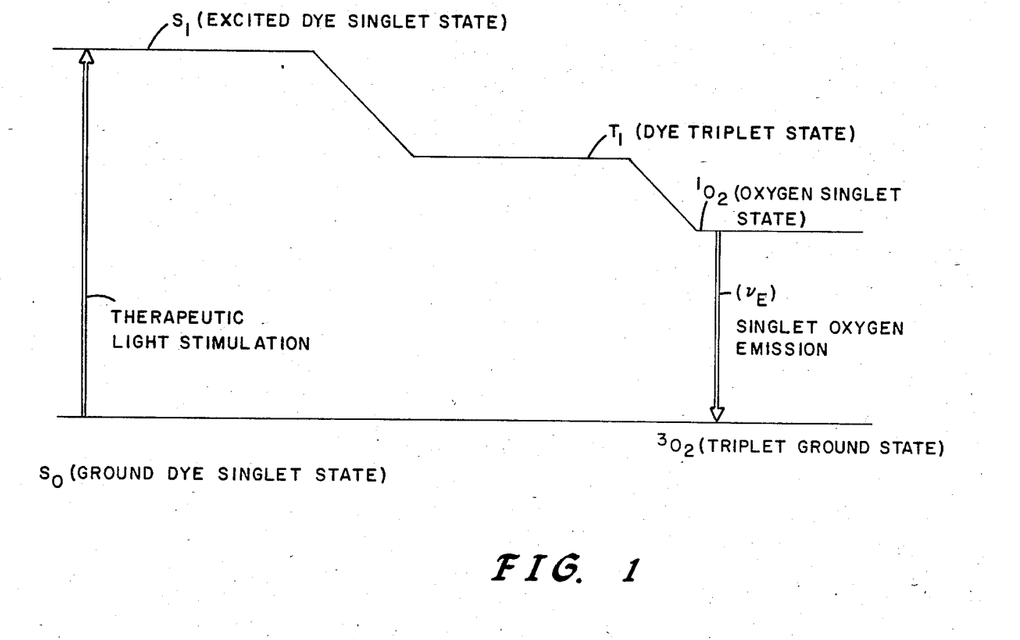
FIG. 1 is a diagram illustrating the overall system kinetics, showing a pulsed excitation light stimulating a photodynamic sensitizer and the resulting generation of singlet oxygen.

Photoradiation therapy involves injecting a patient with a non-toxic photodynamic sensitizer, such as hematoporphyrin derivative, and after the sensitizer has localized at the appropriate biological site, illuminating that site with optical energy. The resulting photodynamic action causes singlet oxygen to be generated in a two-step process. FIG. 1 illustrates schematically the overall system kinetics. First the photodynamic sensitizer is excited from the ground state, $S_o$, to the first excited electronic state, $S_1$, by means of a therapeutic light source, such as pulsed laser radiation at 6300 angstroms (red light). The sensitizer excited singlet state $S_1$ is then transformed via an intramolecular coupling to the lowest-lying dye triplet state, $T_1$, as indicated in the figure. Subsequent deactivation of this triplet state to the ground singlet state, $S_0$, in the absence of oxygen, is forbidden by the spin selection rules, resulting in lifetimes of this particular species under anaerobic (oxygen-excluded) conditions as long as one millisecond. However, in the presence of oxygen localized in the tissue, the dye triplet, $T_1$, will deactivate rapidly (1 to 10$\mu$ sec) to the dye singlet ground state, $S_0$, in a spin-conserving intramolecular process in which essentially all the energy in the dye triplet is transferred to the triplet electronic state of oxygen, $^3O_2$, raising the latter to the first excited electronic singlet state, $^1O_2$, approximately 1 electron-volt above the ground state. This spin-conserving energy transfer is possible only because the ground electronic state of molecular oxygen happens to be a triplet which is not true for most stable molecules. This energy transfer, which is shown in FIG. 1, can be represented as follows:

$$T_1 + {}^3O_2 \rightarrow S_0 + {}^1O_2 \tag{1}$$

When subject oxygen, $^1O_2$, interacts with molecules contained in the surrounding medium M, a relatively weak collisionally induced emission occurs:

$$^1O_2 + M \rightarrow {}^3O_2 + M + h\nu_E \tag{2}$$

The quantity $\nu_E$ is the frequency associated with the center of the emission band and corresponds to a wavelength of 1.27 microns. (The singlet oxygen emission band is centered at 1.27$\mu$ and has a full-width-half-maximum (FWHM) extending from 1.26$\mu$–1.28$\mu$. This band shall hereafter be referred to as the singlet oxygen 1.27 micron emission band or the 1.27$\mu$ band.) By optically detecting and monitoring this emission it is possible to determine the instantaneous rate at which singlet oxygen is being generated and is attacking biological matter.

Figure 2:
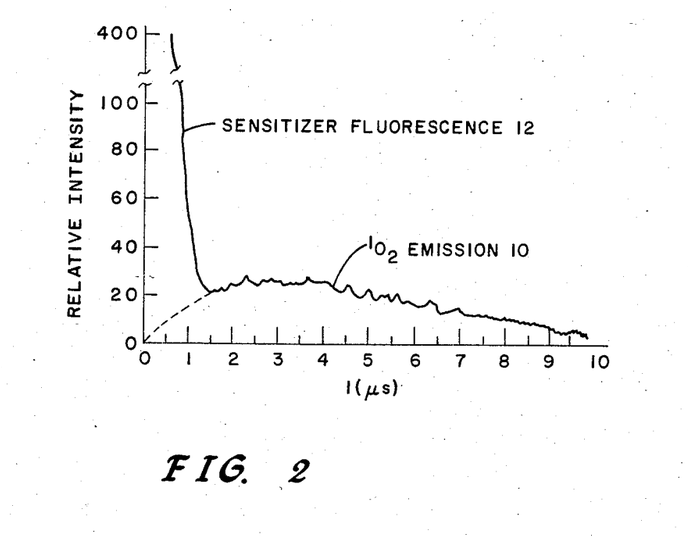
FIG. 2 is a graph showing the composite sensitizer fluorescence/singlet oxygen emission signal appearing in the 1.27 micron band.

The optical energy emitted in the 1.27$\mu$ emission band during photodynamic therapy is a composite signal comprising a first component due to the spectrally diffuse fluorescence of the sensitizer and a second component produced by the spectrally discrete emission from singlet oxygen molecules. FIG. 2 illustrates the results of experimental measurements of the composite signal in the 1.27$\mu$ band. Both the singlet oxygen $^1O_2$ emission (10) and the sensitizer fluoroscence (12) arise as a consequence of optical excitation of the sensitizer and both appear in the 1.27$\mu$ emission band. The sensitizer fluorescence in the 1.27$\mu$ band is in general much larger in magnitude than the relatively weak singlet oxygen emission. As shown in FIG. 2, the peak amplitude of the sensitizer fluorescence reaches a relative intensity of 400 as compared to a maximum singlet oxygen emission intensity of 25.

The central difficulty to be overcome, therefore, in monitoring the singlet oxygen emission is to separate this component from that due to the sensitizer fluorescence. Applicants have discovered that the composite signal can be separated by signal processing in the time domain. This processing utilizes the fact that the sensitizer fluorescence is simultaneous with that of the exciting light while the appearance of the singlet oxygen emission is delayed in time. This time delay is due to the fact that formation of the singlet oxygen is not directly coupled to the optical excitation. Formation of $^1O_2$ involves a collisionally induced transfer of energy from the sensitizer metastable triplet state, and is thus delayed with respect to the initiation of the optical excitation by the time required to bring about collision of the ground electronic state dissolved oxygen $^3O_2$ with the excited sensitizer. This collision time is dependent on the diffusion rate of $^3O_2$ in the particular solvent, as well as the ambient $^3O_2$ concentration level (i.e., $^3O_2$ solubility). Some solvents are characterized by high oxygen solubility and diffusion rates (e.g., ethanol, methanol, acetone) with characteristics sensitizer triplet energy transfer times in the range of 0.20–0.30$\mu$ sec; however, others notably $H_2O$ and $D_2O$, involve significantly longer times (2–3$\mu$ sec) and in the extreme cases of high solvent viscosity (i.e., low diffusion rates) and low oxygen solubility, times of the order of 10$\mu$ sec are involved (e.g., ethylene glycol).

Absorption of the incident optical excitation energy leads to the essentially instantaneous formation of an initial sensitizer triplet concentration $[T_1]_o$. Transfer of this energy to ground triplet state oxygen takes place according to Eq. (1) described above.

Quantitatively, Equation (1) may also be expressed in the form:

$$d[T_1]/dt = \alpha J - K_T[^3O_2][T_1] \tag{3}$$

where $J = J(t)$ is the time-dependent incident light flux expressed in photons/cm$^2$ second, $\alpha$ is the sensitizer absorption coefficient expressed in cm$^{-1}$. In most cases depletion of ground state oxygen is unimportant, i.e., $[^1O_2] << [^3O_2]$, in which case Eq. (3) may be written as follows:

$$d[T_1]/dt = \alpha J - k_T[T_1] \tag{4}$$

in which $$k_T = K_T[^3O_2]$$

represents the rate of transfer of energy from the sensitizer triplet to $^3O_2$ to form $^1O_2$. The rate of increase of $[^1O_2]$ is given by the following equation:

$$d[^1O_2]/dt = k_T[T_1] - k_D[^1O_2] \tag{6}$$

with $k_D$ denoting the rate of loss of $^1O_2$ due to collisions with the solvent molecules (or molecular complexes).

The general solution of Eq. (4) is as follows:

$$[T_1] = \alpha e^{-k_T t} \int_0^t J(s) e^{k_T s} ds. \quad (7)$$

For pulsed excitation in the form of a square-wave, we have $$J(t) = \begin{cases} 0; & t < 0 \\ J_o; & 0 < t < \tau, \\ 0; & t > \tau \end{cases} \quad (8)$$

where $J_o$ is constant.

Substitution of Eq. (8) into Eq. (7) gives $$[T_1] = \begin{cases} 0; & t < 0 \\ \dfrac{\alpha J_o}{k_T}(1 - e^{-k_T t}); & 0 < t < \tau \\ \dfrac{\alpha J_o}{k_T}(1 - e^{-k_T \tau}) e^{-k_T t}; & t > \tau \end{cases} \quad (9)$$

If we now impose the above stated restriction that $k_T \tau << 1$, and confine our attention to the case $t > Y$, Eq. (9) becomes $$[T_1] = \alpha I_o e^{-k_T t} = [T_1]_o e^{-k_T t} \quad (10)$$

in which $I_o = J_o \tau$ is the total number of incident photos contained in the exciting pulse and $[T_1]_o$, therefore, is the initial concentration of sensitizer triplets.

Combination of Eqs. (6), (10) yields $$[^1O_2] = [T_1]_o \left[ \dfrac{k_T}{k_T - k_D} \right] (e^{-k_D t} - e^{-k_T t}). \quad (11)$$

The temporal behavior indicated by Eq. (11) involves an initial buildup, rising from zero, to a peak and a final phase in which a steady exponential decline takes place. In the event $k_T > k_D$, i.e., rate of triplet energy transfer exceeds the solvent decay rate, the initial phase is characterized by a risetime $Y_R = 1/k_T$ and the ultimate decay by a falltime $Y_F = 1/k_D$. On the other hand, if $k_T < k_D$, the two are reversed, and the risetime is now $Y_R = 1/k_D$ with the falltime $Y_F = 1/k_T$.

A comparison of experimental data shown in FIG. 2 verifies the predictions of Eq. (11). To produce the results shown in FIG. 2 a T4MPP (tetra-4-N methylpyridil porphin) sensitizer was used at a concentration of $1 \times 10^{-4}$M, with the solvent being $H_2O$. Examination of FIG. 2 clearly reveals a two-component behavior with the sensitizer fluorescence existing as a sharply rising (off-scale) early component which decays equally rapidly to negligible levels in a time interval of the order of $1\mu$ sec. The $^1O_2$ signal rises steadily, reaching a maximum after 3-4 $\mu$sec, and then undergoes a steady decline. From this FIG. 2, it is also clear that as far as magnitude is concerned, the early sensitizer fluorescence component is dominant. The ability to separate out the more slowly varying $^1O_2$ component depends strongly on the fact that the detector response time is sufficiently rapid to follow the initial spike to zero after the exciting pulse is extinguished. This places a premium on detector response time. The inventors suggest a fast diode having a Detector Decay Time Constant of 0.2 $\mu$sec (i.e., the return or decay response should fall off by 1/e in 0.2 $\mu$sec. and to less than 1% of maximum in 1 $\mu$sec). The inventors have found an Indium-Gallium-Arsenide (InGaAs) back-illuminated photodiode to be useful in this application. In earlier investigations using a germanium photodiode with a characteristically inferior time resolution, it was impossible to separate the two emission components. Consideration of the of the time history of the data presented in FIG. 2 suggests that the best way to separate the $^1O_2$ emission from the sensitizer IR fluorescence in the time domain is by delaying the box-car aperture (sampling interval) sufficiently in time that the fluorescence component has effectively vanished and that the $^1O_2$ emission has reached a maximum, i.e., approximately 3 $\mu$sec.

Figure 3:
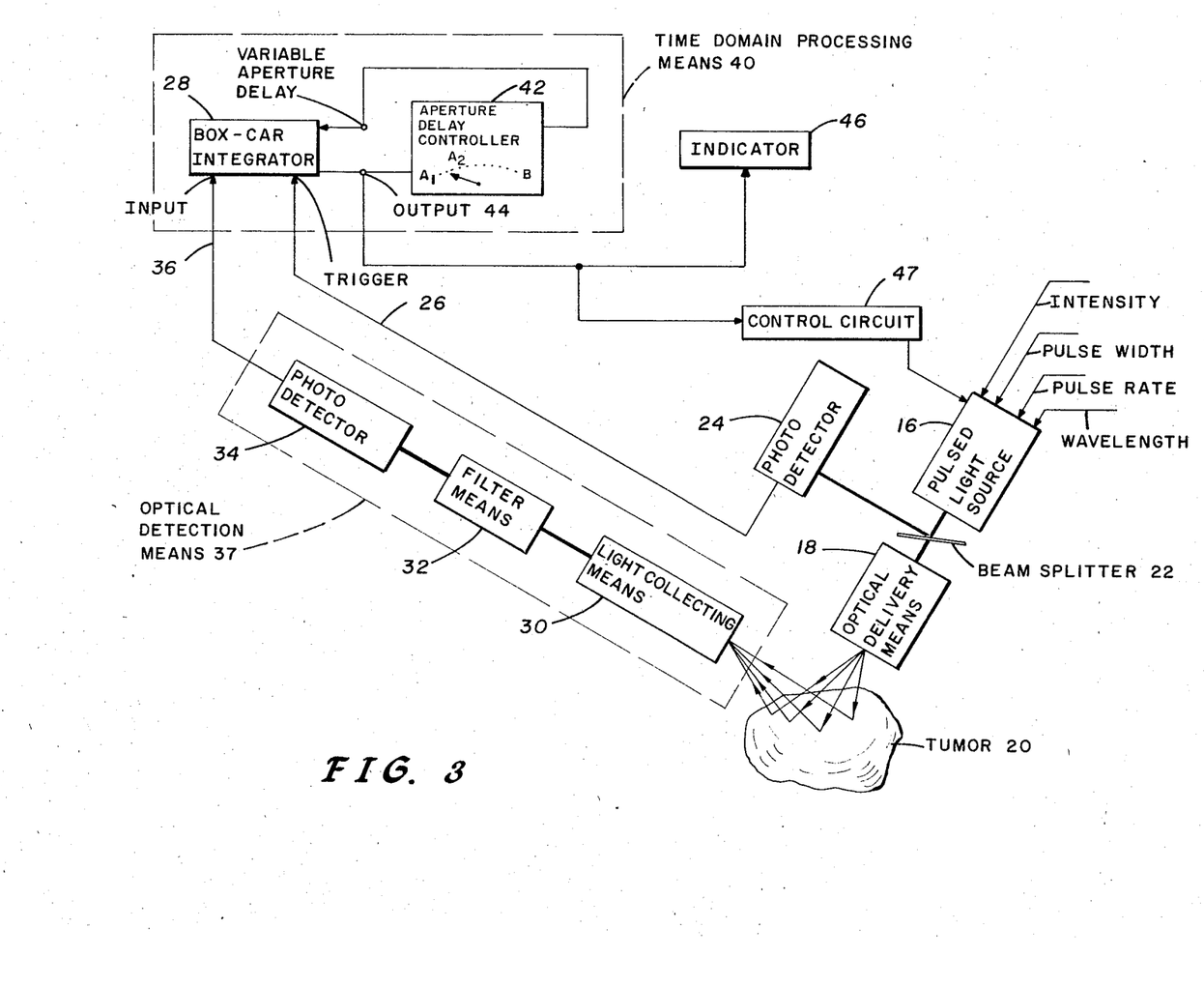
FIG. 3 illustrates, in block diagrammatic form, the invented apparatus used to process the composite sensitizer fluorescence/singlet oxygen emission signal in the time domain so as to extract the singlet oxygen emission signal.

FIG. 3 is block diagrammatic view of the apparatus in accordance with the present invention. A pulsed light source 16 is directed by an optical means 18 onto a biological mass 20. The inventors used a Q switched Nd:YAG laser operating in the second harmonic (5320 Å) to generate a pulse having a 10 nanosecond pulse width; however, any equivalent light source generating a pulse width less than 1 microsecond and at the appropriate excitation wavelength (5,000–7,000 Å) can be used. The optical means 18 used to direct the pulse excitation light can be a lens arrangement or a fiberoptic link.

A beam splitter 24 and a photodiode 26 work in conjunction to produce a reference signal 36, which is used to trigger the box-car integrator 28. Alternatively, an electrical signal produced directly by the excitation pulsing circuit can act as a reference signal 26, synchronizing the box-car integrator to the pulsed interval of the excitation beam.

The biological mass or tumor 20 has absorbed a photodynamic sensitizer, such as hematoporphyrin derivative, and which when irradiated will emit a composite signal composed of a sensitizer fluorescence component and a singlet oxygen emission component. A light collecting means 30, which may be a lens arrangement or a fiberoptic link, collects the light. The collected light is then filtered by filter means 32 which passes light in the singlet oxygen 1.27 micron emission band. (The inventors have used a bandpass filter having 3 dB points at 1.26 micron and 1.28 micron; however, any narrow bandpass filter which passes the 1.27 micron singlet oxygen emission signal will be adequate.) The filtered light is then directed to a photodetector 34 which converts the composite sensitizer fluorescence singlet oxygen emission signal, both appearing in the 1.27 micron emission band, into an electrical signal 36. The light collecting means 30, filter means 32, and photodetector 34 comprise an optical detection means 37. The inventors have found that a "fast" photodiode is necessary to temporally resolve the fast sensitizer infrared fluorescence and the delayed singlet oxygen emission. The detector should have a Detector Time Decay constant of less than 0.2 microseconds (i.e., the return or decay response should fall off by 1/e in less than 0.2 microseconds and to less than 1% of maximum in 1 $\mu$sec.) The inventors have found an Indium Gallium Arsenide (InGaAs) back-illuminated photodiode useful in this application.

The electrical signal 36 is processed by a time domain processing means 40. The time domain processing means 40 includes a box-car integrator 28, and a controller 32. (In certain cases, where the time delay can be set to a particular value, the controller 42 can be eliminated.) The controller 42 can be set to provide a particular aperture time delay (A1, A2, etc.) or it can be set in the scanning mode (B). In the scanning mode, the controller reads the box-car integration output value 44 and moves the box-car aperture across a range of time delay values. The controller, as shall be described below, periodically scans across a range of delay values and locks on the value producing the largest output. The box-car output 44 is connected to indicator 46 where it is displayed.

Figure 4:
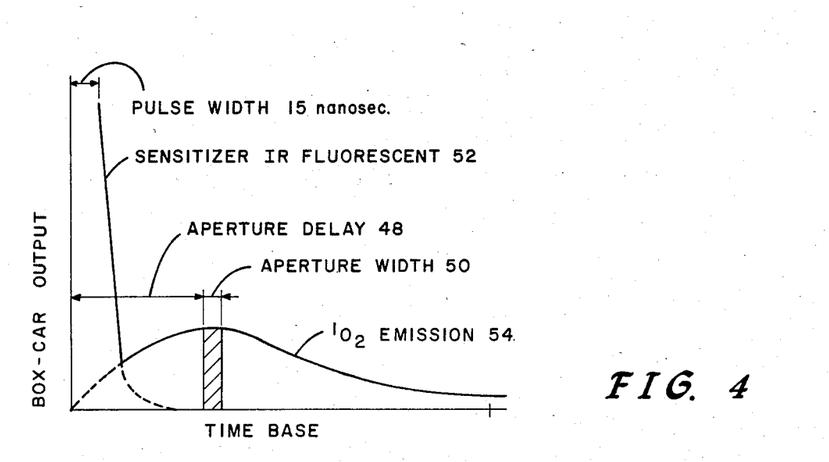
FIG. 4 is a graph showing possible settings of the box-car delay and aperture width used in the present invention for separating the composite signal in the time domain.

FIG. 4 is a graph which describes the various adjustable parameters associated with the time domain signal processor. The box-car integrator (28 see FIG. 3), can be set to a particular box-car delay 48 and to a particular aperture width 50. The inventors have found that a delay of 1 to 1.5 microseconds from the trailing edge of the excitation pulse should be the minimum in a biological environment. The inventors have used a 0.5 microsecond aperture width to generate the data shown graphically in FIG. 2; however, it is to be understood that other aperture widths within a range of 0.10 to 1.0 microseconds can be used in a biological environment depending on the particular composition. It is to be further understood, that the box-car delay 48 is to be selected so that only a minimal level of sensitizer fluorescence signal 52 enters into the box-car for integration. Selection of the box-car delay 48 allows the time domain processor to extract the singlet oxygen signal 54 from the composite fluorescence/singlet oxygen emission signal.

Figure 5:
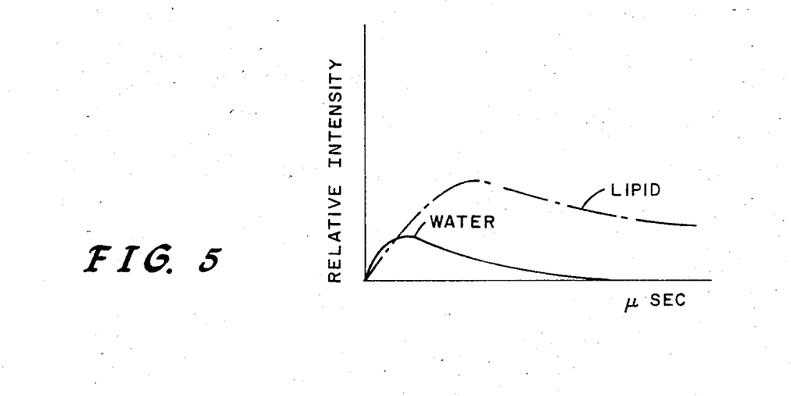
FIG. 5 is a graph showing the singlet oxygen emission curves for singlet oxygen generated in water and lipid media.

In addition to isolating the singlet oxygen signal from the sensitizer fluorescence in the time domain, the present inventive technique can be used to distinguish between the maximum singlet oxygen signal produced in different biological media. As shown earlier in Eq. (11), the shape of the singlet oxygen emission curve is determined by the particular medium (i.e., aqueous or lipid) in which the singlet oxygen is generated. As shown in FIG. 5, for an aqueous medium, the singlet oxygen lifetime is short and the maximum emission appears at approximately 3 microseconds (within the range 2-4 microseconds); for a lipid medium, on the other hand, the singlet oxygen lifetime is longer (within the range 10-40 microseconds); however, triplet energy transfer times tend also to be longer so that in general the emission reaches a maximum later in time. By adjusting the aperture delay, one can separate the maximum singlet oxygen emission generated in the lipid from the maximum singlet oxygen emission signal generated in an aqueous environment. Therefore, one can preset the box-car delay to detect a maximum singlet oxygen signal generated in a particular solvent. Alternatively, one can scan the aperture delay across a selected range and measure the corresponding outputs. In a biological environment, having a complex mixture of aqueous and lipid components (for example), one can periodically scan across a range of aperture delays to assure that the maximum output is being recorded.

Figure 6:
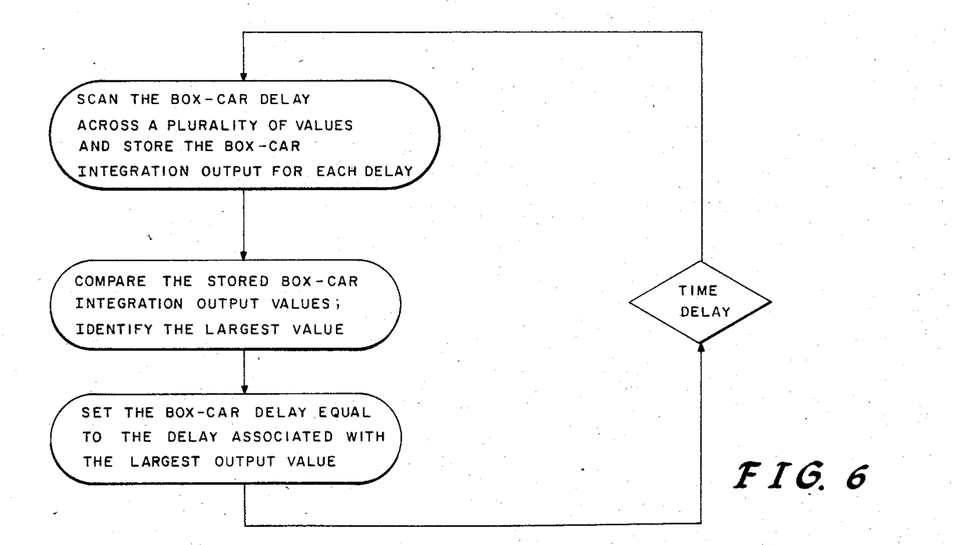
FIG. 6 is a flow chart showing the operation of a microprocessor controller used to select the appropriate box-car delay.

Referring to FIG. 3, the controller 42 can be set to scan the box-car delay across the range of values and select the values producing the a maximum output. The controller may be of a conventional microprocessor design and perform the following functions more specifically shown in the flow chart in FIG. 6: (1) scan the box-car delay across a plurality of values and record the corresponding output for each delay value; (2) compare the output values and select the largest; (3) set the aperture delay to the value which produced the largest output; and, (4) periodically scan the box-car delay to select the one producing the largest output.

Control circuit 47 is electrically coupled to said controller 42 and adjusts operational parameters of the pulsed light source 16 in response to changes in the maximum singlet oxygen signal output. Control circuit 47 is of conventional microprocessor design and adjusts the intensity, pulse rate, pulse width, and wavelength of said pulsed light source 16 to maintain the maximum signal oxygen emission level either at a stable value or above a certain minimum value. In any event, if the maximum singlet oxygen emission value falls to zero, the control circuit 47 shuts off the pulsed light source 16.

Figure 7:
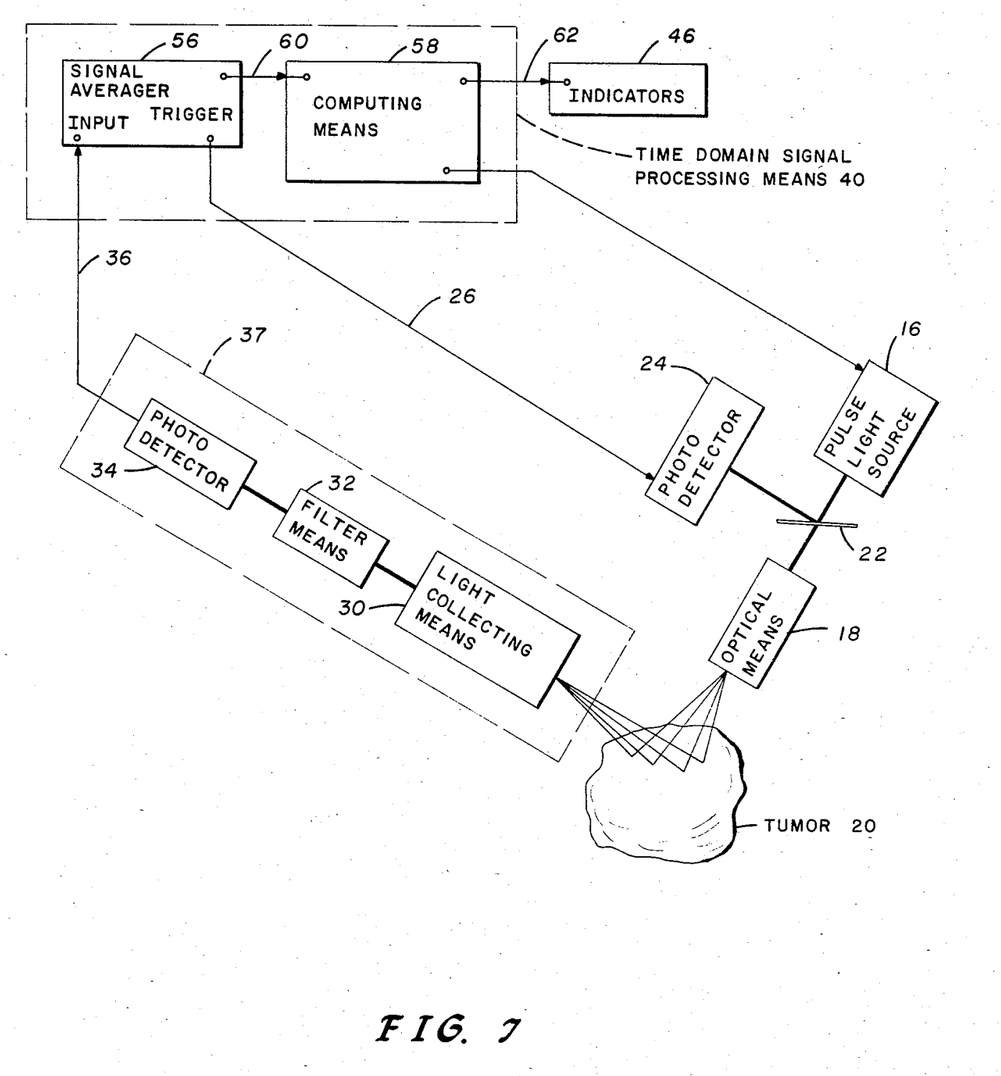
FIG. 7 illustrates, in block diagrammatic form, an alternate time domain signal processing means as taught by the present invention.

FIG. 7 is a block diagrammatic view of an alternative embodiment which uses a signal averager 56 as a component in the time domain signal processing means 40. The apparatus comprises: a pulsed light source 16 and an optical means 18 for delivering appropriate pulsed excitation to the biological mass 20; an optical detection means 37 including a light collection means 30, filter means 32 and photodetector 34—the optical detection means provides an electrical output signal 36 proportional to the intensity of the composite two-component signal produced in the 1.27 micron band; and, a time domain signal processor 40 for processing the electrical signal 36 and providing as output the singlet oxygen emission level which is displayed on indicator 46. The time domain signal processor 40 may include a single averager 56 and a computing means 58. The inventors have used a model 1170 Nicolet signal averager, although other commercially available signal averagers will work equally well. A signal averager acts like a box-car integrator except that it has a plurality of apertures or time bins (addresses). The signal averager is triggered at the pulse excitation rate and records a time history of the emission over a preselected number of excitation pulses. The time bins corresponding to the first 1 to 1.5 microseconds following the pulse excitation decay are dominated by the sensitizer fluorescence. The remaining time bins contain the time history of the desired singlet oxygen emission signal. The time history of the singlet oxygen emission signal can be displayed directly—i.e., output 60 from the signal averager can pass directly to an indicator 46 which will display time bins occurring 1 to 1.5 microseconds after the excitation pulse decay. Alternatively, computing means 40 can process the raw time history data 60 and provide as output the total singlet oxygen emission produced in a complex media such as biological mass. It will be remembered that a biological mass is a complex mixture of aqueous and lipid components; each producing a different singlet oxygen emission curve.

Data corresponding to the digitized time history 60 is transferred to the computing means 58, where it is analyzed. The first step in the analysis is to discard the data from time bins corresponding to the first 1 to 1.5 microseconds which is dominated by the sensitizer fluorescence. The remaining data then contains the time history of the singlet oxygen emissions. While the singlet oxygen emission is spread out over a certain period of time, in which the signal reaches a peak and then decays, the value of emission corresponding to the total singlet oxygen emission $[^1O_2]_o$ may be recovered in addition to the value of the peak emission by a numerical regression analysis using Eq. (11). It is important to obtain this value since the measured peak emission will vary with the local values of the rate of formation and decay of singlet oxygen which may change during therapy. $[^1O_2]_o$ on the other hand, is a measure of the amount of singlet oxygen formed by energy transfer from the sensitizer triplet state independently of how fast it forms or decays.

The regression analysis involves the use of a numerical search procedure that seeks to choose the values of the parameters $k_T$, $k_D$, and $[^1O_2]_o = [T_1]_o$ in such a way as to maximize the sum of the square of deviations between the measured and computed values of the singlet oxygen emission. The method used for the regression is based on Marquardt's method for solving nonlinear regression problems (D. W. Marquardt, *J. Soc. Indust. Appl Math.* 11, 431 (1963)), incorporated herein by reference.

Once the value of $[^1O_2]_o$ is calculated it can be displayed at indicator 46. The computing means can also use the $[^1O_2]_o$ value to generate commands to vary the operational parameters of the pulsed light source 16—it may vary light intensity, pulse duration, wavelength, etc.

Figure 8:
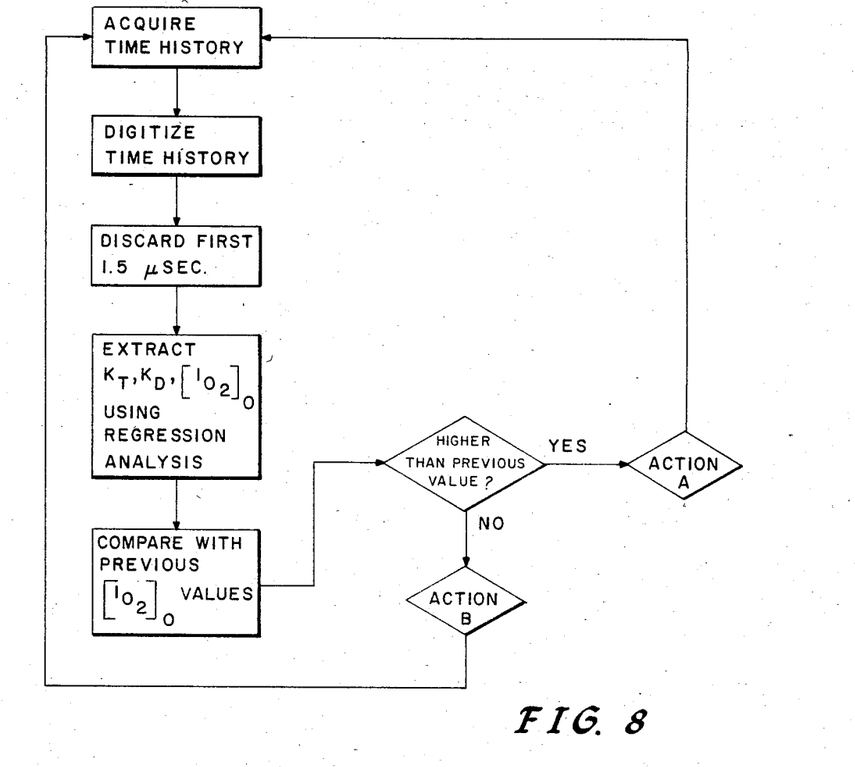
FIG. 8 is a flow chart of a regression analysis data processing routine used to calculate the total singlet oxygen emission $[^1O_2]_o$ based on digitized time history.

The computing means 58 can be of known microprocessor circuit design and can be programmed to perform the software functions as shown in FIG. 8. In general, at certain preselected intervals, the computing means will calculate a new $[^1O_2]_o$ and compare it with the previous value. On the basis of the results of this comparison, appropriate changes in the operating parameters of the light delivery system would be made. Such actions would include: (1) termination of therapy because localized oxygen has been depleted and singlet oxygen is no longer being produced; (2) lower the intensity of the excitation pulse, or adjust the pulse width or pulse rate so that singlet oxygen can be generated at a rate which will avoid oxygen depletion; (3) shift the wavelength of the light.

Although calculation of the available total singlet oxygen production $[^1O_2]_o$ by the above technique has been described in the context of photochemotherapy, it is to be understood that it could also be effective to measure the total singlet oxygen emission in any biological or other complex environment having two or more components, wherein each components produces different singlet oxygen lifetimes.

Figure 9:
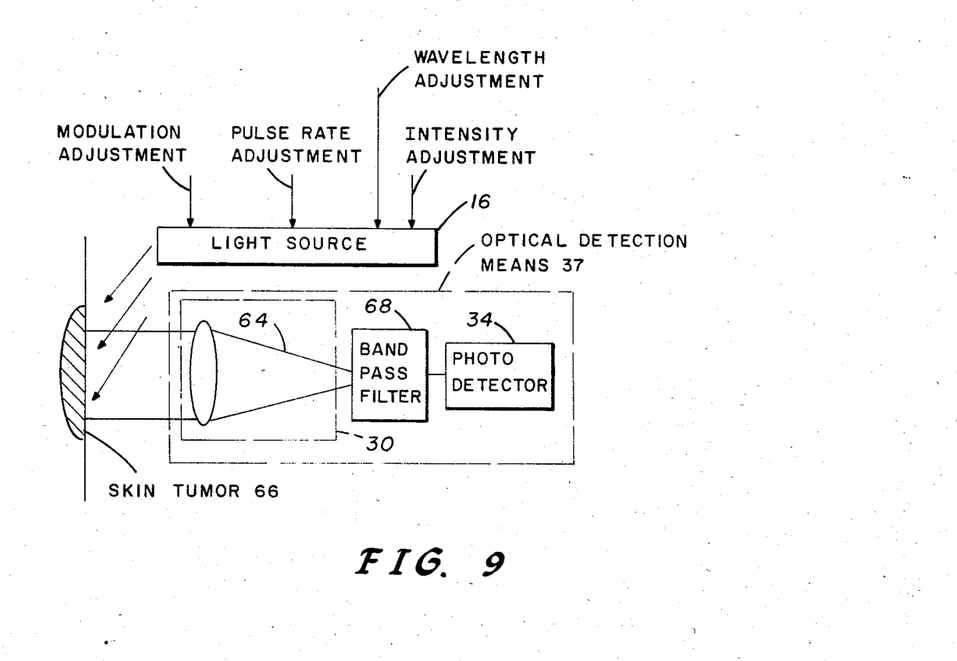
FIG. 9 is the light collecting means for collecting the composite signal emitted from a surface or skin tumor.
Figure 10:
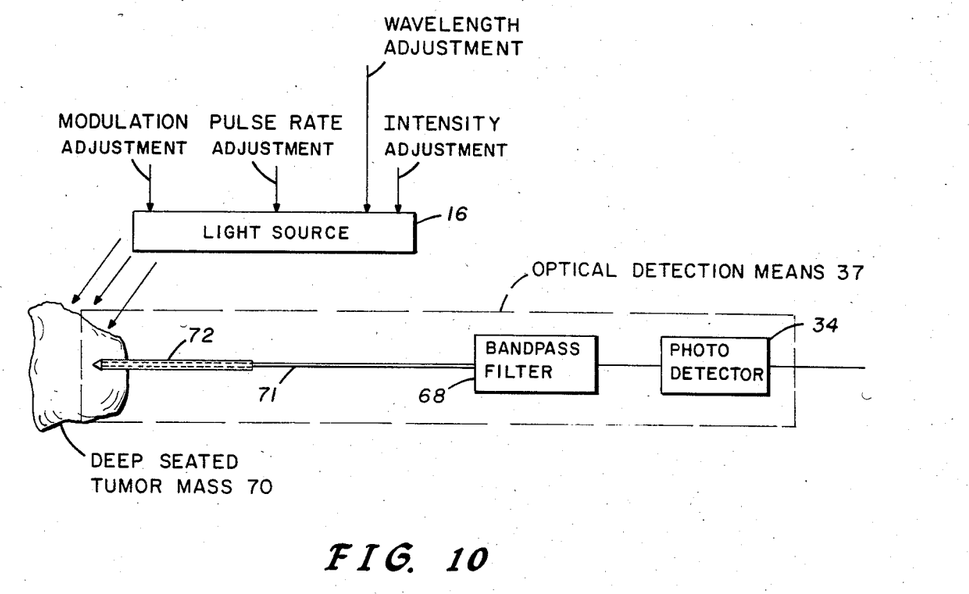
FIG. 10 is the light collecting means for collecting the composite signal emitted from a deep seated tumor mass.
Figure 11:
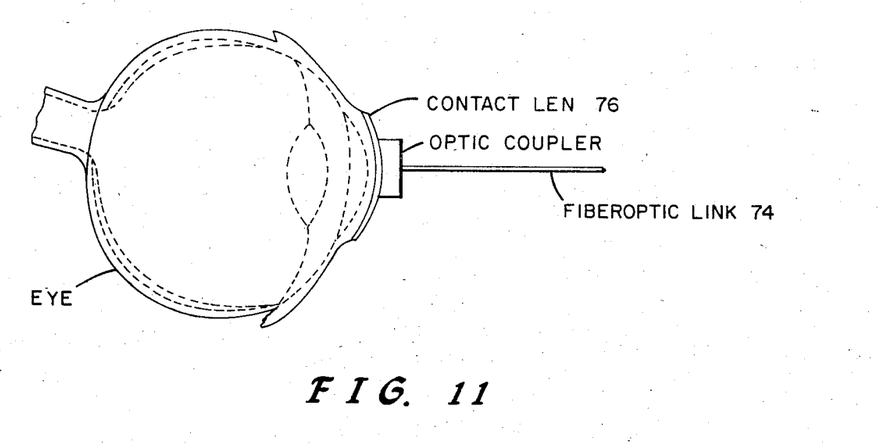
FIG. 11 is the light collecting means for collecting the composite signal emitted from an ocular tumor.

FIGS. 9, 10 and 11 show various light collection means 30 and light delivery means contemplated by the inventors. In FIG. 8, the lens arrangement 64 collects light emitted by a surface or skin tumor 66 and focuses the emitted light through filter 68 onto the photodetector 34. FIG. 10 shows an alternative embodiment used in the treatment of deep seated tumors. A fiberoptic wave guide 71 is inserted into the tumor mass 70 and directs collected light to the filter 68. The fiberoptic wave guide 71 can be inserted into tumor mass 70 through a hollow hypodermic needle 72. A single fiberoptic probe could be used to direct the pulsed excitation light into the tumor mass and also to collect and transmit collected emissions to the photodetector 34. FIG. 11 shows an alternative embodiment used in the treatment of eye tumors. A fiberoptic link 71 is optically coupled to a contact lens 76 rather than inserted into the tumor area. The contact lens arrangement generally contains a contact lens which is placed over the cornea and optically coupled to a fiberoptic link. The contact lens fiberoptic link combination collects the emitted light and transmits it to the optical detection means.

The current invention has many applications where singlet oxygen is measured in a biological environment or other environments where the singlet oxygen emission signal is masked by the sensitizer fluorescent signal. Applicants have discovered that one such application is in monitoring the effectiveness of photochemotherapy, alternatively referred to as photoradiation therapy or photodynamic therapy all of which are to be considered equivalent. Current photochemotherapy treatment involves intravenous injection of the patient with hematoporphyrin derivative or compounds thereof. After two to three days the hematoporphyrin derivative sensitizer has been selectively retained by the tumor tissue. Photoradiation is then used to excite the sensitizer to its singlet state to produce singlet oxygen within the malignant tissue. The therapeutic light may penetrate directly through the patient's skin into the tumor area if the tumor is located relatively close to the surface. For deep-seated or large tumors, a system employing fiberoptics may be used which allows delivery of the light to any desired depth within the tumor. The therapeutic light can also be delivered by various types of endoscopes to the cervix, bronchus, bladder, etc.

Prior photoradiation therapy light delivery systems required the physician to guess the correct therapeutic light dosage. If the dosage is too high, normal tissue will experience necrosis; and, if the dosage is insufficient, the tumor will not be destroyed. Since the physician has no way of knowing the rate at which oxygen is being delivered to the tissue or the magnitude of the local photodynamic sensitizer concentration, it is impossible to predict the effect of a given therapeutic light dosage. If the light dosage is too intense, local oxygen may be depleted more rapidly than is provided to the tissue and no additional singlet oxygen will be generated for any increase in intensity or duration of the light dosage. The only adequate way to prescribe the therapeutic light dosage therefore is by direct monitoring of the level of singlet oxygen produced.

The present invention provides a means for direct monitoring of the singlet oxygen concentration produced during photochemotherapy. The singlet oxygen level displayed by indicator 46 (see FIGS. 3 and 7) is a direct measure of singlet oxygen concentration. If the singlet oxygen signal drops significantly, it indicates to the physician the need to modify the excitation light dosage (i.e., local oxygen depletion has probably occurred). The physician can adjust the intensity, duration, or modulation of the excitation beam to maximize the singlet oxygen production, and thereby insure the effectiveness of photochemotherapy. Also by recording the box-car integrator output as a function of aperture delay or observing the time history of the singlet oxygen concentration, a physician can determine certain average properties of the tumor mass. In short, the preset invention gives the physician means for monitoring, in real time, the amount of singlet oxygen generated in the tumor mass and provides a means for quantitative measurement of treatment effectiveness.

Obviously many modifications and variations of the present invention are possible in light of the above teachings. It is therefore to be understood that within the scope of the appended claims the invention may be practiced otherwise than is specifically described.

What is claimed and desired to be secured by Letters Patents of the United States is:

1. An apparatus for detecting singlet oxygen emission produced during photoradiation:
   an optical excitation means for illuminating a portion of a medium containing a photodynamic sensitizer with intermittent intervals of optical excitation radiation;

an optical detection means for collecting light emitted from said medium and for detecting a composite emission signal in the 1.27 micron singlet oxygen emission band, whereby said composite signal includes a sensitizer fluorescent signal component and a singlet oxygen emission signal component, said sensitizer fluorescent signal component occurring essentially concurrently with said optical excitation radiation and said singlet oxygen emission signal component occurring at a time delayed from the occurrence of said optical excitation radiation;

a time domain processing means, operably coupled to said optical detection means, for temporally separating said singlet oxygen emission signal component from said sensitizer fluorescent signal component, and, a responsive means operably associated with said time domain processing means for indicating the magnitude of said singlet oxygen emission signal component.

2. The apparatus of claim 1, wherein said time domain processing means includes means for integrating said composite signal in a narrow time window between excitation intervals and over a plurality of said intermittent intervals of optical excitation radiation, said narrow time window selectively placed a certain time interval from the trailing edge of each of said intervals of optical excitation radiation.

3. The apparatus of claim 2, wherein said time window is selectively placed at least 1 microsecond from the trailing edge of each of said intervals of optical excitation radiation.

4. The apparatus of claim 1, wherein said time domain processing means comprises a box-car integrator means for integrating over time said composite emission signal during a plurality of said intermittent intervals of optical excitation radiation, said box-car integrating means having an aperture delay greater than the decay time of said sensitizer fluorescent component.

5. The apparatus of claim 1, wherein said time domain processing means includes a box-car integrator means for integrating said composite emission signal between excitation intervals and over a plurality of said intermittent intervals of optical excitation radiation, said box-car integrator means having an aperture delay of at least 1 microsecond from the trailing edge of each of said intermittent intervals of optical excitation radiation, so that only a minimum level of said sensitizer fluorescence signal component will be selectively integrated.

6. The apparatus of claim 1, wherein said time domain signal processor comprises a signal averager means for integrating said composite signal between excitation intervals and over a plurality of said intermittent intervals of optical excitation radiation, said signal averager means having a plurality of time bins, wherein time bins corresponding to the first microsecond following the trailing edge of each said intermittent intervals of optical excitation radiation will be dominated by said sensitizer fluorescence signal component; and time bins occurring more than one microsecond after the trailing edge of said intermittent interval optical excitation radiation will be dominated by the singlet oxygen emission signal component.

7. The apparatus of claim 1, wherein said responsive means further includes means for adjusting the operable characteristics of said optical excitation means in response to the magnitude of the singlet oxygen signal component.

8. The apparatus of claim 1, wherein said optical excitation comprises pulses of optical excitation radiation, and wherein said time domain processing means comprises a box-car integrator.

9. The apparatus of claim 8, further comprising a triggering means, operably connected to said box-car integrator, for synchronizing said box-car integrator with each of said pulses of optical excitation radiation and wherein said box-car integrator includes means for integrating said composite emission signal produced between pulses and over a plurality of pulses of said optical excitation radiation.

10. The apparatus of claim 9, wherein said box-car integrator has an aperture delay value greater than the decay time of said sensitizer fluorescent component.

11. The apparatus of claim 9, wherein said box-car integrator has an aperture delay value of at least 1 microsecond from the trailing edge of each of said pulse of optical excitation radiation.

12. The apparatus of claim 11, wherein said time domain processing means further includes a controller means for scanning said aperture delay across a plurality of values, for storing the output from said box-car integrator means corresponding to each aperture delay value, and for determining and setting the aperture delay value corresponding to the largest output from said box-car integrator means, thereby determining an optimum aperture delay.

13. The apparatus of claim 12, wherein said controller means further includes a means for periodically determining an optimum aperture delay and for setting said box-car integrator means to said optimum aperture delay for a set period of time.

14. The apparatus of claim 12, wherein said aperture delay ranges from 1 to 20 microseconds.

15. The apparatus of claim 12, wherein said responsive means further includes means for adjusting the operable characteristics of said optical excitation means in response to the magnitude of the singlet oxygen signal component.

16. The apparatus of claims 11, wherein said box-car integrator means has an aperture width in the range 0.1 to 1.0 microseconds.

17. The apparatus of claim 1, wherein said optical excitation comprising pulses of optical excitation radiation, and wherein said time domain signal processor comprises a signal averaging means, having a plurality of time bins for integrating a time history of said composite signal during a plurality of pulses of said optical excitation radiation, whereby time bins occurring more the one microsecond following the trailing edge of each said pulses of optical excitation radiation will be dominated by the singlet oxygen signal component; and, wherein said apparatus further includes a triggering means, operably connected to said signal averaging means for synchronizing said signal averaging means with each of said pulses of said optical excitation radiation.

18. The apparatus of claim 17, wherein at least one of said time bins occurring at least 1 microsecond following the trailing edge of said pulses of optical radiation is coupled to said responsive means, and wherein said responsive means includes means for indicating the signal level of said at least one time bin.

19. The apparatus of claim 17, wherein said time domain signal processor further includes a computing means for processing raw data from each of said plurality of time bins and for calculating the total singlet oxygen emission level $[^1O_2]_o$ wherein said total singlet oxygen emission level $[^1O_2]_o$ is a measure of the amount of singlet oxygen formed by energy transfer from the sensitizer triplet state independently of how fast the singlet oxygen emission signal forms or decays.

20. The apparatus of claim 19, wherein said responsive means includes means for indicating the total singlet oxygen emission level $[^1O_2]_o$.

21. The apparatus of claim 19, wherein said computing means includes,
 a first means for acquiring time history data from said signal averaging means;
 a second means for digitizing said time history data;
 and a third means for discarding said time history data occurring in time bins corresponding to the first microsecond following a trailing edge of each of said pulses of optical excitation radiation.

22. The apparatus of claim 21, wherein said computing means further includes:
 a fourth means for calculating total singlet oxygen emission level $[^1O_2]_o$ by numerical regression analysis using the following equation:

$$[^1O_2] = [T_1]_o \left[ \frac{k_T}{k_T - k_D} \right] (e^{-k_D t} - e^{-k_T t}).$$

23. The apparatus of claim 22, wherein said responsive means includes means for indicating the total singlet oxygen emission level value $[^1O_2]_o$.

24. The apparatus of claim 22, wherein said computing means further includes a fifth means for comparing the calculated total singlet oxygen level $[^1O_2]_o$ with a previously calculated value of total singlet oxygen emission level $[^1O_2]_o$.

25. The apparatus of claim 24, wherein said computing means is a microprocessor.

26. The apparatus of claim 24, wherein said computing means further includes a sixth means for shutting off said optical excitation means when the total singlet oxygen emission level $[^1O_2]_o$ equals zero.

27. The apparatus of claim 24, wherein said computing means further includes a sixth means for adjusting the intensity of said optical excitation means to maintain a stable total singlet oxygen emission level $[^1O_2]_o$.

28. The apparatus of claim 24, wherein said computing means further includes a sixth means for adjusting the pulse width of said optical excitation means to maintain a stable total singlet oxygen emission level $[^1O_2]_o$.

29. The apparatus of claim 24, wherein said computing means further includes a sixth means for adjusting the pulse rate of said optical excitation means to maintain a stable total singlet oxygen emission level $[^1O_2]_o$.

30. The apparatus of claim 24, wherein said computing means includes a sixth means for adjusting the wavelength of said optical excitation means to maintain said total singlet oxygen level $[^1O_2]_o$ above a certain limit.

31. The apparatus of claim 8 or 17, wherein said optical excitation means includes:
 a pulsed light source; and,
 an optical means, operably associated with said pulsed light source, for directing said pulses of optical excitation radiation onto said medium containing said photodynamic sensitizer.

32. The apparatus of claim 31, wherein said optical means is a fiberoptic link adapted for insertion into a tumor mass.

33. The apparatus of claim 31, wherein said optical means is a lens arrangement.

34. The apparatus of claim 31, wherein said pulsed light source includes means for generating light at a wavelength 5,000–7,000 Angstroms.

35. The apparatus of claim 31, wherein said pulse light source includes means for generating pulses having a pulse width less than 1 microsecond.

36. The apparatus of claim 31, wherein said pulsed light source is a laser.

37. The apparatus of claim 31, wherein said pulsed light source is a Q switched Nd:YAG laser operating in the second harmonic (5320 Angstroms).

38. The apparatus of claims 9 or 17, wherein said triggering means includes:
 a photodetector means for generating an electrical impulse in response to each of said pulses of optical excitation radiation.

39. The apparatus of claim 1, wherein said optical detection means includes:
 a light collecting means for collecting light emitted from said medium;
 a filter means for passing optical radiation in the 1.27 micron singlet oxygen emission band; and,
 a photodetector means for generating an electrical signal corresponding in intensity to the optical radiation passed by said filter means.

40. The apparatus of claim 39, wherein said photodetector means is a photodiode having sufficient temporal resolution to resolve both the sensitizer fluorescence signal component and the singlet oxygen emission signal component.

41. The apparatus of claim 39, wherein said photodetector means is a photodiode having a decay response which falls off by 1/e in less than 0.2 microseconds and to less than 1% in 1 microsecond.

42. The apparatus of claim 39, wherein said photodetector means is a photodiode having a detector decay response constant of 0.2 microseconds.

43. The apparatus of claim 39, wherein said photodetector means is an Indium Galium Arsenide/Indium Phosphide (InGaAs/InP) back illuminated photodiode.

44. The apparatus of claim 39, wherein said filter means is a narrow band pass filter which passes optical radiation in the 1.27 micron singlet oxygen emission band.

45. The apparatus of claim 44, wherein said narrow band pass filter as 3 dB points at 1.26 micron and 1.28 micron.

46. The apparatus of claim 1, wherein said light collecting means is a fiberoptic waveguide adapted to be inserted into a tumor mass.

47. The apparatus of claim 1, wherein said light collecting means is a fiberoptic waveguide mounted in a hollow hypodermic needle, and wherein said hollow hypodermic needle is adapted to be inserted into a tumor mass.

48. The apparatus of claim 1, wherein said light collecting means is a lens arrangement.

49. The apparatus of claim 1, wherein said light collecting means includes a fiberoptic link optically connected to a contact lens, and wherein said contact lens is adapted to be fit on the eye of a patient.

50. A method for detecting singlet oxygen emission produced during photoradiation:

illuminating at least a portion of a medium containing a photodynamic sensitizer with intermittent intervals of optical excitation radiation;

collecting light emitted from said medium;

filtering said collected light to pass optical energy in the 1.27 micron single oxygen emission band;

generating an electrical signal corresponding in intensity to said filtered light, whereby said electrical signal is a composite signal having a sensitizer fluorescent signal component and a singlet oxygen emission signal component;

processing said composite signal in the time domain to temporally separate said sensitizer fluorescent signal component occurring essentially concurrently with said optical excitation radiation from said singlet oxygen emission signal component occurring at a time delayed from the occurrence of said optical excitation radiation; and, generating an output signal indicating the magnitude of said singlet oxygen emission.

51. The method of claim 50, wherein said processing step involves the step of integrating said composite signal between intermittent intervals and over a plurality of intermittent intervals of said optical excitation radiation.

52. The method of claim 51, wherein said integrating step involves integrating said composite signal in a narrow time window.

53. The apparatus of claim 52, when said integrating step further includes the step of selectively positioning said time window a certain time interval from the trailing edge of each of said intervals of optical excitation radiation.

54. The method of claim 53, further involving the step of setting said time interval to a value greater than the decay time of said sensitizer fluorescent signal component.

55. The method of claim 53, further including the step of setting said time interval to a value at least 1 microsecond from the trailing edge of each intermittent interval of said optical excitation radiation.

56. The method of claim 50, wherein said processing step involves the step of integrating said composite signal in a plurality of narrow time windows located at a different time interval from the trailing edge of each intermittent interval of said optical excitation radiation.

57. The method of claim 50, wherein said intermittent intervals of optical excitation radiation are pulses of optical excitation radiation and wherein said processing step further involves:

integrating said composite signal between pulses and over a plurality of pulses of said optical excitation radiation using a box-car integrator;

triggering said box-car integrator in synchronization with each of said pulses of optical excitation radiation; and setting said box-car integrator aperture delay to a value greater than the decay time of said sensitizer fluorescent component signal, whereby said box-car integrator generates an output signal indicating the magnitude of said singlet oxygen emission.

58. The method of claim 57, wherein said box-car integrator aperture delay is set to a value at least 1 microsecond from the trailing edge of each of said pulses of optical excitation radiation.

59. The method of claim 58, further including the step of:

scanning said box-car integrator aperture delay across a plurality of values;

storing the output from said box-car integrator corresponding to each of said box-car integrator aperture delay values;

comparing said stored output values; and, selecting the optimum aperture delay by determining the aperture delay corresponding to the largest output value.

60. The method of claim 59, further involving the steps of periodically selecting the optimum aperture delay and setting said box-car integrator to said optimum aperture delay for a certain period of time.

61. The method of claim 58, wherein said processing step further involves the step of scanning said box-car integrator aperture delay to selectively integrate a portion of said singlet oxygen emission signal component.

62. The method of claim 50, wherein said intermittent intervals of optical excitation radiation are pulses of optical excitation radiation, and wherein said processing step further involves:

integrating a time history of said composite signal in a plurality of time bins using a signal averager;

triggering said signal averager in synchronization with each of said pulses of optical excitation radiation.

63. The method of claim 62, wherein said processing step further includes the step of selecting at least one time bin occurring at least 1 microsecond from the trailing edge of each of said pulses of optical excitation radiation, whereby such selected time bins contain magnitude information on the singlet oxygen emission component.

64. The apparatus of claim 62, further comprising the steps of:

acquiring time history data from said time bins digitizing said time history data;

discarding said time history data from time bins corresponding to the first 1 microsecond following a trailing edge of each of said pulses of optical radiation; and, calculating the total singlet oxygen emission level $[^1O_2]_o$ by numerical regression analysis of the following equation:

$$[^1O_2] = [T_1]_o \left[ \frac{k_T}{k_T - k_D} \right] (e^{-k_Dt} - e^{-k_Tt}).$$

65. A method for determining the singlet oxygen emission signal level produced in a complex medium involving the steps of:

illuminating at least a portion of a complex medium containing a photodynamic sensitizer with pulses of optical excitation radiation;

collecting light emitted from said medium;

filtering said collective light to block optical energy substantially outside of the 1.27 micron singlet oxygen emission band;

generating an electrical signal corresponding in intensity to said filtered light, whereby said electrical signal is a composite signal having a sensitizer fluorescent component and at least one singlet oxygen emission component signal corresponding to each medium of said complex medium mixture;

integrating said composite signal over a narrow time window occurring at least 1 $\mu$sec from the trailing edge each of said pulses of optical excitation radiation; and, regulating said time interval to permit selective integration of a portion of said singlet oxygen emission component.

66. The method of claim 65, wherein said complex medium is a biological medium containing aqueous and lipid components and wherein said regulating step further involves adjusting said time interval in the range of 2.0–4.0 microseconds until a maximum integration signal is obtained in said narrow time window, whereby said maximum signal represents the maximum singlet oxygen emission signal produced from the aqueous component of said biological medium.

67. The method of claim 65, wherein said complex medium is a biological medium containing aqueous and lipid components and wherein said regulating step further involves adjusting said time interval in the range 5.0–15.0 microseconds until a maximum integration signal is obtained in said narrow time window, whereby said maximum signal represents the maximum singlet oxygen emission signal produced from the lipid component of said biological medium.

68. The apparatus of claim 67, wherein said integrating step involves the step of integrating with a box-car integrator and said regulating step involves adjusting the aperture delay of said box-car integrator.

69. A method for controlling the effectiveness of therapeutic photoradiation of cancer tissue which has previously absorbed a photosensitizing dye, comprising the steps of illuminating at least a portion of said cancer tissue with pulses of optical excitation radiation;

collecting light emitted from said cancer tissue;

filtering said collected light to black optical energy substantially outside of the 1.27 micron singlet oxygen emission band;

generating an electrical signal corresponding in intensity to said filtered light, whereby said electrical signal is a composite signal having a sensitizer fluorescent signal component and a singlet oxygen emission signal component;

processing said composite signal in the time domain and temporally separating said sensitizer fluorescent signal component occurring essentially concurrently with said optical excitation radiation from said singlet oxygen emission signal component occurring at a time delayed from the occurrence of said optical excitation radiation;

evaluating said singlet oxygen emission component signal in the time domain to determine at least one characteristic of said singlet oxygen emission component signal; and, adjusting at least one operational parameter of said pulses of optical excitation radiation in accordance with changes in said at least one characteristic of said singlet oxygen emission component signal.

70. The method of claim 69, wherein said processing step involves integrating said composite signal between pulses and over a plurality of pulses of optical excitation radiation using a signal averager and wherein said evaluating step further involves the steps of:

acquiring time history data from said signal averager;

digitizing said time history date;

selecting said time history data occurring more than one microsecond following the trailing edge of each of said pulses of optical excitation radiation;

calculating the total singlet oxygen emission level $[^1O_2]_o$ by numerical regression analysis from said selected data.

71. The method of claim 70, wherein said adjusting step involves shutting off said pulses of optical excitation radiation when said total singlet oxygen emission level $[^1O_2]_o$ equals zero.

72. The method of claim 70, wherein said adjusting step involves adjusting the intensity of said pulses of optical excitation radiation to maintain said total singlet oxygen emission level $[^1O_2]_o$ above a certain limit.

73. The method of claim 70, wherein said adjusting steps involves adjusting the pulse width of said pulses of optical excitation radiation to maintain said total singlet oxygen emission level $[^1O_2]_o$ above a certain limit.

74. The method of claim 70, wherein said adjusting step involves adjusting the wavelength of said pulses of optical excitation radiation to maintain said total singlet oxygen emission level $[^1O_2]_o$ above a certain limit.

75. The method of claim 69, wherein said processing step involves integrating said composite signal between pulses and over a plurality of pulses of optical excitation radiation using a box-car integrator, and wherein said evaluation step further involves the steps of:

changing the aperture delay of said box-car integrator to a value in excess of 1 microsecond until a maximum singlet oxygen emission signal results.

76. The method of claim 75, wherein said adjusting step involves the step of shutting off said pulses of optical excitation radiation when said maximum singlet oxygen emission level equals zero.

77. The method of claim 75, wherein said adjusting step involves the step of adjusting the intensity of said pulses of optical excitation radiation to maintain said maximum singlet oxygen emission level above a certain limit.

78. The method of claim 75, wherein said adjusting step involves the step of adjusting the pulse width of said pulses of optical excitation radiation to maintain said maximum singlet oxygen emission level above a certain limit.

79. The method of claim 75, wherein said adjusting step involves the step of adjusting the pulse rate of said pulses of optical excitation radiation to maintain said maximum singlet oxygen emission level above a certain limit.

80. The method of claim 75, wherein said adjusting step involves adjusting the wavelength of said pulses of optical excitation radiation to maintain said maximum subject oxygen emission level above a certain limit.

* * * * *

UNITED STATES PATENT AND TRADEMARK OFFICE
CERTIFICATE OF CORRECTION

PATENT NO. : 4,592,361
DATED : June 3, 1986
INVENTOR(S) : Parker et al

Page 1 of 2

It is certified that error appears in the above-identified patent and that said Letters Patent is hereby corrected as shown below:

In the references:

Column 1, line 27, delete "Biofizaka" and substitute therefor -- Biofizika --.

Column 2, line 1, delete "Sedden" and substitute therefor -- Seddon --.

Column 2, line 3, delete "Clanton" and substitute therefor -- Clayton --.

Column 2, line 7, delete "Doiven" and substitute therefor -- Doiron --.

In the specifications:

Column 9, line 44, delete "$Y_R$" and substitute therefor -- $t_R$ --.

Column 9, line 45, delete "$Y_F$" and substitute therefor -- $t_F$ --.

Column 9, line 47, delete "$Y_R$" and substitute therefor -- $t_R$ --.

Column 9, line 47, delete "$Y_F$" and substitute therefor -- $t_F$ --.

UNITED STATES PATENT AND TRADEMARK OFFICE
CERTIFICATE OF CORRECTION

PATENT NO.  : 4,592,361

DATED       : June 3, 1986

INVENTOR(S) : Parker et al

It is certified that error appears in the above-identified patent and that said Letters Patent is hereby corrected as shown below:

In the claims:

Column 16, line 53, delete "the" preceding "one" and substitute therefor -- than --.

Column 21, line 24, delete "67" and substitute therefor -- 65 --.

Signed and Sealed this

Twenty-fifth Day of November, 1986

Attest:

DONALD J. QUIGG

Attesting Officer    Commissioner of Patents and Trademarks